United States Patent [19]
Bhambhani et al.

[11] Patent Number: 6,143,286
[45] Date of Patent: Nov. 7, 2000

[54] METHOD FOR IMPROVING THE FADE RESISTANCE OF HAIR AND RELATED COMPOSITIONS

[75] Inventors: Malti Vishin Bhambhani, Scotch Plains; Alexander Chan, Cranbury, both of N.J.; Geoffrey Robert Hawkins, Langhorne, Pa.

[73] Assignee: Revlon Consumer Products Corporation, New York, N.Y.

[21] Appl. No.: 09/129,922

[22] Filed: Aug. 5, 1998

[51] Int. Cl.[7] .............................. A61K 7/06; A61K 7/075
[52] U.S. Cl. ...................... 424/70.1; 424/70.1; 424/70.2; 424/70.6; 424/70.11; 424/70.12; 424/70.19; 424/70.28; 424/407; 514/880; 514/881
[58] Field of Search .................. 424/401, 70.1, 424/70.2, 70.6, 70.12, 70.122, 70.17, 70.27, 70.28, 70.31; 514/880, 881

[56] References Cited

U.S. PATENT DOCUMENTS

| | | | |
|---|---|---|---|
| 4,563,347 | 1/1986 | Starch | 424/70 |
| 4,973,476 | 11/1990 | Krzysik | 424/71 |
| 5,132,443 | 7/1992 | Traver | 556/425 |
| 5,290,545 | 3/1994 | Halloran et al. | 424/70 |
| 5,409,695 | 4/1995 | Abrutyn et al. | 424/70.12 |
| 5,482,703 | 1/1996 | Pings | 454/70.12 |
| 5,662,892 | 9/1997 | Bolich | 424/70.1 |
| 5,955,066 | 9/1999 | Sako et al. | 424/70.12 |

OTHER PUBLICATIONS

International Cosmetic Ingredient Dictionary and Handbook, Seventh Edition, vol. 1, pp. 73–74.

*Primary Examiner*—Thurman K. Page
*Assistant Examiner*—Lakshmi Channavajjala
*Attorney, Agent, or Firm*—Julie Blackburn

[57] ABSTRACT

Hair conditioning compositions comprising 0.1–20% cationic conditioning agent, 0.1–30% fatty alcohol, 0.001–10% nonionic surfactant, 0.001–20% of a polysiloxane having D and T units, wherein the ratio of D units to T units in the polysiloxane is about 10 to 80 D units for every T unit; and 5–95% water; as well as a method for improving the fade resistance of color treated hair comprising applying to the hair an aqueous based hair care composition containing one or more hair treating active ingredients and a siloxane having D and T units, wherein the ratio of D units to T units in the siloxane is about 10 to 80 D units for every T unit.

9 Claims, No Drawings

METHOD FOR IMPROVING THE FADE RESISTANCE OF HAIR AND RELATED COMPOSITIONS

TECHNICAL FIELD

The invention is in the field of compositions for application to hair, and methods for treating hair to achieve improved, long lasting conditioning and shine, as well as improving the fade resistance of color treated hair.

BACKGROUND OF THE INVENTION

Hair color is very popular today. A large percentage of women and men dye their hair, particularly at the time when the hair begins to gray. Hair can be colored with semi-permanent dyes which wash out within six to eight shampoos. On the other hand, oxidative dye systems are used for permanent coloration of hair. Even though oxidative dyes are referred to as permanent, hair colored in this manner tends to fade after multiple shampooings, with red tones being particularly susceptible. Thus, a consumer who has dyed her hair with oxidative dye may notice color fading, sometimes even after only one or two weeks. There is a need for compositions and methods to improve the fade resistance of color treated hair.

In addition, even for those who do not color their hair, it is desireable to have shiny, healthy-looking hair. Products which improve hair shine are very popular with consumers, particularly product which provide long lasting shine.

One object of the invention is to provide a hair conditioning composition which provides long lasting conditioning to hair fibers and improves the fade resistance of color treated hair.

Another object of the invention is to provide a method for treating colored hair which causes the hair to exhibit improved resistance to fading after one or more shampooings.

Another object of the invention is provide a method for improving the shine of hair by treating the hair with a hair conditioining composition.

Another object of the invention is provide hair conditioning compositions which improve hair shine and improve the fade resistance of color treated hair.

SUMMARY OF THE INVENTION

The invention comprises a hair conditioner composition comprising, by weight of the total composition:
- 0.1–20% cationic conditioning agent,
- 0.1–30% fatty alcohol,
- 0.001–10% nonionic surfactant,
- 0.001–20% of a polysiloxane having D and T units, wherein the ratio of D units to T units in the polysiloxane is about 10 to 80 D units for every T unit; and
- 5–95% water.

The invention also comprises a method for improving the fade resistance of color treated hair comprising applying to the hair an aqueous based hair care composition containing one or more hair treating active ingredients and a polysiloxane having D and T units, wherein the ratio of D units to T units in the polysiloxane is about 10 to 80 D units for every T unit.

The invention also comprises a method for improving hair shine comprising applying to the hair an aqueous based hair conditioner composition comprising (a) a polysiloxane having D and T units wherein the ratio of D units to T units in the polysiloxane is about 10 to 80 D units for every T unit; and (b) a silicone of the formula:

$$A\text{---Si}(R)(R)\text{---O}\left[\text{---Si}(R)(R)\text{---O}\right]_x\left[\text{---Si}(R)(R')\text{---O}\right]_y\text{---Si}(R)(R)\text{---A}$$

wherein R and R' are each independently alkyl, or aryl, and x and y are each independently 0–100,000 with the proviso that there is at least one of either x or y, and A is siloxy endcap unit.

DETAILED DESCRIPTION

All percentages mentioned herein are percentages by weight unless otherwise indicated. In addition:

The term "color treated hair" means hair that has been dyed with oxidative dyes which are comprised of at least one primary intermediate and at least one coupler for the formation of oxidation dyes.

The term "fade resistance" means that the color treated hair exhibits reduced color fading after shampooing with traditional cleansing surfactant-based shampoos.

The term "hair treating active agent" means an agent which generally provides a substantive effect on hair fibers such as conditioning, cleansing, coloring, or permanent waving. For example, cationic surfactants or polymers are hair treating active agents which provide conditioning effect to hair fibers when used in shampoos, conditioners, and the like. In another example, anionic or amphoteric surfactants are hair treating active agents which provide cleansing effect to hair fibers when used in shampoos.

The compositions of the invention provide long lasting conditioning to hair, improve hair shine, and additionally, provide improved fade resistance when used on color treated hair.

In the method of the invention, the fade resistance of color treated hair is substantially improved by applying to the hair an aqueous based hair care composition containing one or more hair treating active ingredients and an organosiloxane polymer having D and T units, wherein the ratio of D units to T units in the siloxane is about 10 to 80 D units for every T unit.

In the method of the invention, hair shine is noticeably improved by applying the hair conditioning compositions of the invention.

THE COMPOSITIONS OF THE INVENTION

Cationic Conditioning Agent

The compositions of the invention comprise 0.1–20%, preferably 0.5–15%, more preferably 1–12% by weight of the total composition of a cationic conditioning agent.

Suitable cationic conditioning agents are cationic polymers, quaternary ammonium salts or the salts of fatty amines. Quaternary ammonium salts have the formula:

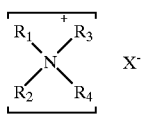

wherein $R_1$, $R_2$, $R_3$, and $R_4$ are each independently an aliphatic group of 1 to 22 carbon atoms, or aromatic, alkyl, aryl, or alkaryl group having 12 to 22 carbon atoms; with the proviso that there is at least one alkyl group having 12 to 22 carbon atoms. Preferably at least one of $R_1$, $R_2$, $R_3$, and $R_4$ are methyl while the remaining substituents are $C_{12-22}$ aliphatic radicals. X is an anion selected from halogen, acetate, phosphate, nitrate and methyl sulfate, tosylate, and hydroxide radicals. The aliphatic groups may contain, in addition to carbon atoms, ether linkages as well as amido groups. Suitable quaternary ammonium compounds may be mono-long chain alkyl, di-long chain alkyl, tri-long chain alkyl, and the like. Examples of such quaternary ammonium salts include behenalkonium chloride, behentrimonium chloride, behentrimonium methosulfate, benzalkonium chloride, benzethonium chloride, benzyl triethyl ammonium chloride, cetalkonium chloride, cetrimonium chloride, cetrimonium bromide, cetrimonium methosulfate, cetrimonium tosylate, cetylpyridinium chloride, dibehenyl/diarachidyl dimonium chloride, dibehenyldimonium chloride, dibehenyldimonium methosulfate, dicapryl/dicaprylyl dimonium chloride, and the like.

Other quaternary ammonium salts useful as the cationic conditioning agent are compounds of the general formula:

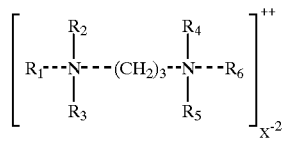

wherein at least one of $R_{1-6}$ is an aliphatic group having 16 to 22 carbon atoms, and the remaining $R_{1-6}$ are the same or different and are selected from alkyls having 1 to 4 carbon atoms and X is an anion as above defined.

Amides which exhibit the general formulas set forth below are also suitable conditioning agents:

wherein R is a straight or branched chain saturated or unsaturated alkyl having 6 to 30 carbon atoms, n is an integer from 1 to 4, and X and Y are each independently H, or $C_{1-6}$ alkyl.

Preferred is an amide of the formula:

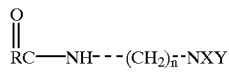

wherein R is a $C_{12-22}$ straight or branched chain alkyl, n is an integer from 1 to 4, and X is lower alkyl, preferably methyl.

Also suitable are amidoamine salts, which are the condensation products of fatty acids with a polyfunctional amines, for example, those having the formula $RCONH(CH_2)_nNR_1R_2$ where RCO is a fatty acyl group such as stearoyl, $R_1$ and $R_2$ are methyl or ethyl, and n is 2 or 3. Examples of such compounds include stearamidopropyl dimethylamine. Particularly preferred are amidoamine compounds complexed with a mild dimer acid, such as di(behenamidopropyl dimethyl amine) dimer dilinoleate or di(linoleamidopropyl dimethyl amine) dimer linoleate. Both ingredients are sold by Alzo, Inc. under the NECON tradename.

Also, quaternary imidazolinium salts having the following general formula are suitable as the cationic conditioning agent:

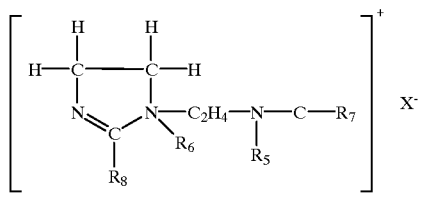

wherein $R_5$ is hydrogen or a $C_{1-4}$ alkyl; $R_6$ is a $C_{1-4}$ alkyl; $R_7$ is a $C_{8-22}$ alkyl; and $R_8$ is hydrogen, or a $C_{1-22}$ alkyl; and X is an anion as defined above.

Also suitable as the cationic hair conditioning agent are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine, ethyl stearamine, and so on.

Also suitable as the cationic conditioning agent are cationic polymers such as:

(a) quaternary derivatives of cellulose ethers such as polymers sold under the tradename JR-125, JR-400, JR-30M.

(b) copolymers of vinylpyrrolidone having monomer units of the formula:

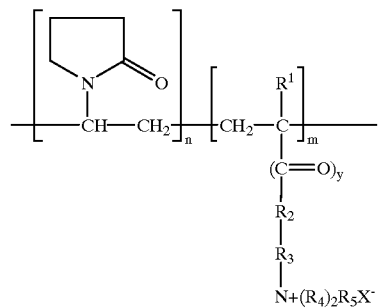

wherein $R^1$ is hydrogen or methyl, preferably methyl;
y is 0 or 1, preferably 1
$R^2$ is O or NH, preferably NH;
$R^3$ is $C_xH_{2x}$ where x is 2 to 18, or —$CH_2$—CHOH—$CH_2$—, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

(c) Homopolymer of dimethyidiallylammonium chloride, or copolymer of dimethyldiallylammonium chloride and acrylamide. Such compounds are sold under the tradename MERQUAT by Merck.

(d) Homopolymers or copolymers derived from acrylic or methacrylic acid, selected from monomer units acrylamide, methylacrylamide, diacetone-acrylamide, acrylamide or methacrylamide substituted on the nitrogen by lower alkyl, alkyl esters of acrylic acid and methacrylic acid, vinylpyrrolidone, or vinyl esters.

(e) cationic silicones. As used herein, the term "cationic silicone" means any silicone polymer or oligomer having a silicon backbone, including polysiloxanes, having a positive charge on the silicone structure itself. Cationic silicones that may be used in the compositions of the invention include those corresponding to the following formula, where the ratio of D to T units, if present, are greater than about 80 D units to 1 T unit:

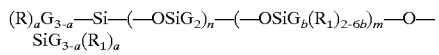

in which G is selected from the group consisting of H, phenyl, OH, $C_{1-10}$ alkyl, and is preferably $CH_3$; and a is 0 or an integer from 1 to 3, and is preferably 0; b is 0 or 1, preferably 1; the sum n+m is a number from 1 to 2,000 and is preferably 50 to 150; n is a number from 0 to 2000, and is preferably 50 to 150; and m is an integer from 1 to 2000, and is preferably 1 to 10; R is a $C_{1-10}$ alkyl, and $R_1$ is a monovalent radical of the formula $C_qH_{2q}L$ in which q is an integer from 2 to 8 and L is selected from the groups:

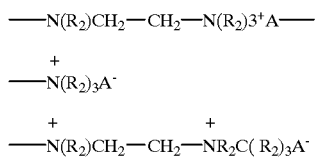

in which $R_2$ is selected from the group consisting of H, phenyl, benzyl, a saturated hydrocarbon radical, and is preferably an alkyl radical containing 1–20 carbon atoms; and A– is a halide, methylsulfate, or tosylate ion.

(f) polymeric quaternary ammonium salts such as Polyquaternium 31, 33, 34, 35, 36, 37, and 39.

Also suitable are diquaternary polydimethylsiloxanes such as Quaternium-80, sold by Goldschmidt Corporation under the tradename ABIL-Quat 3272.

Examples of other cationic polymers that can be used in the compositions of the invention are disclosed in U.S. Pat. Nos. 5,240,450 and 5,573,709, which are hereby incorporated by reference.

The preferred compositions of the invention contain 0.5–15% by weight of a cationic conditioning agent which is selected from the group:

(a) quaternary ammonium salts have the formula:

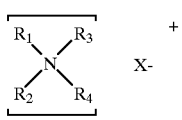

wherein $R_1$ is an aliphatic group of 1 to 22 carbon atoms, or aromatic, aryl, or alkaryl group having 12 to 22 carbon atoms; $R_2$ is an aliphatic group having 1–22 carbon atoms; $R_3$ and $R_4$ are each alkyl groups of from 1 to 3 carbon atoms, and X is an anion selected from halogen, acetate, phosphate, nitrate, methyl sulfate, tosylate, and hydroxide radicals;

(b) cationic silicones having the following formula, wherein the ratio of D to T units is greater than 80 to 1 respectively:

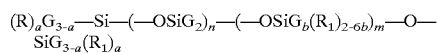

wherein G is H, phenyl, OH, $C_{1-10}$ alkyl; a is 0 or an integer from 1 to 3; b is 0 or 1; the sum n+m is a number from 1 to 2,000; n is a number from 0 to 2000; and m is an integer from 1 to 2000; and $R_1$ is a monovalent radical of the formula $C_qH_{2q}L$ in which q is an integer from 2 to 8 and L is selected from the groups:

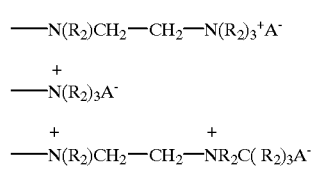

in which $R_2$ is H, phenyl, benzyl, a saturated hydrocarbon radical, and is preferably an alkyl radical containing 1–20 carbon atoms; and A– is a halide ion; and (c) an amide of the formula:

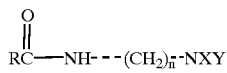

wherein R is a $C_{12-22}$ straight or branched chain alkyl, n is an integer from 1 to 4, and X is lower alkyl, preferably methyl, (d) an amidoamine salt, and mild dimer acids thereof.

Particularly preferred is where the cationic conditioning agent is selected from trimethylsilylamodimethicone (having a D to T ratio of about 100 to 1), cocamidopropyl betaine, cetrimonium chloride, stearamidopropyl dimethylamine, behentrimonium chloride, di(behenamidopropyl dimethyl amine) dimer dilinoleate, di(linoleamidopropyl dimethyl amine) dimer linoleate, or mixtures thereof.

Fatty Alcohol

The hair conditioning compositions used in the method of the invention preferably contain 0.1–20%, preferably 0.5–10%, more preferably 1–8% of a fatty alcohol having the formula $RCH_2OH$ wherein R is a straight or branched chain saturated or unsaturated alkyl having at least about 6 to 30 carbon atoms. Examples of fatty alcohols suitable for use include behenyl alcohol, $C_{9-15}$ alcohols, caprylic alcohol, cetearyl alcohol, coconut alcohol, decyl alcohol, lauryl alcohol, cetyl alcohol, myristyl alcohol, oleyl alcohol, palm alcohol, stearyl alcohol, tallow alcohol, and the like. The preferred compositions of the invention include a mixture of cetyl and stearyl alcohols.

Nonionic Surfactant

The compositions of the invention contain 0.001–10%, preferably 0.01–8%, more preferably 0.01–5% of a nonionic surfactant or emulsifier.

Suitable nonionic surfactants include alkoxylated alcohols, or ethers, formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on. Particularly preferred is Ceteareth 20, which is the reaction product of a mixture of cetyl and stearyl alcohol with ethylene oxide, and the number of repeating ethylene oxide units in the molecule is 20.

Also suitable as the nonionic surfactant are alkyoxylated carboxylic acids, which are formed by the reaction of a carboxylic acid with an alkylene oxide or with a polymeric ether. The resulting products have the general formula:

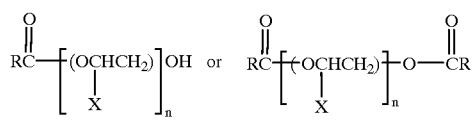

where RCO is the carboxylic ester radical, X is hydrogen or lower alkyl, and n is the number of polymerized alkoxy groups.

In the case of the diesters, the two RCO— groups do not need to be identical. Preferably, R is a $C_{6-30}$ straight or branched chain, saturated or unsaturated alkyl, and n is from 1–100.

Also suitable as the nonionic surfactant are monomeric, homopolymeric and block copolymeric ethers. Such ethers are formed by the polymerization of monomeric alkylene oxides, generally ethylene or propylene oxide. Such polymeric ethers have the following general formula:

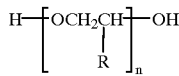

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

Also suitable as nonionic surfactants are silicone surfactants, which are defined as silicone polymers which have at least one hydrophilic radical and at least one lipophilic radical. The silicone surfactant used in the compositions of the invention are organosiloxane polymers that may be a liquid or solid at room temperature. The organosiloxane surfactant is generally a water-in-oil or oil-in-water type surfactant which is, and has an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

HLB=7+11.7×log $M_w/M_o$ where $M_w$ is the molecular weight of the hydrophilic group portion and $M_o$ is the molecular weight of the lipophilic group portion.

Preferably the surfactant is linear silicone of the formula:

$MD_xD'_yD''_zM$ wherein $M=RRRSiO_{1/2}$,
  $D$ and $D'=RR'SiO_{2/2}$,
  $D''=RRSiO_{2/2}$,
  x, y, and z are each independently 0–1000, where R is methyl or hydrogen, and R' is a hydrophilic radical or a lipophilic radical, with the proviso that the compound contains at least one hydrophilic radical and at least one lipophilic radical.

Most preferred is wherein
  M=trimethylsiloxy
  $D=Si[(CH_3)][(CH_2)_nCH_3]O_{2/2}$ where n=0–40,
  $D=Si[(CH_3)][(CH_2)_o—O—PE)]O_{2/2}$ where PE is $(—C_2H_4O)_a(—C_3H_6O)_bH$, o=0–40,
  a=1–100 and b=1–100, and
  $D''=Si(CH_3)_2O_{2/2}$ More specifically, suitable silicone surfactants have the formula:

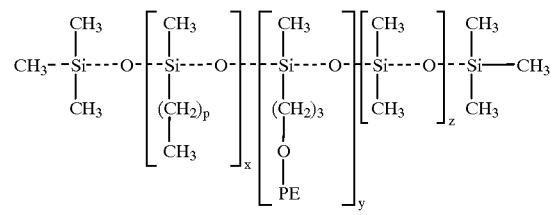

wherein p is 0–40, preferably 12–20, most preferably 15, and PE is $(—C_2H_4O)_a(—C_3H_6O)_b—H$
where x, y, z, a, and b are such that the maximum molecular weight of the polymer is approximately 50,000.

Another type of preferred organosiloxane emulsifier suitable for use in the compositions of the invention are emulsifiers sold by Union Carbide under the Silwet™ trademark. These emulsifiers are represented by the following generic formulas:

wherein PE=—$(EO)_m(PO)_nR$
  R=lower alkyl or hydrogen
  Me=methyl
  EO is polyethyleneoxy
  PO is polypropyleneoxy
  m and n are each independently 1–5000
  x and y are each independently 0–5000, and

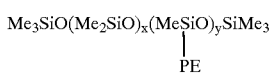

wherein PE=—$CH_2CH_2CH_2O(EO)_m(PO)_nZ$
  Z=lower alkyl or hydrogen, and
  Me, m, n, x, y, EO and PO are as described above,
with the proviso that the molecule contains a lipophilic portion and a hydrophilic portion. Again, the lipophilic portion can be supplied by a sufficient number of methyl groups on the polymer.

Also suitable as nonionic silicone surfactants are hydroxy-substituted silicones such as dimethiconol, which is defined as a dimethyl silicone substituted with terminal hydroxy groups.

Examples of silicone surfactants are those sold by Dow Corning under the tradename Dow Corning 3225C Formulation Aid, Dow Corning 190 Surfactant, Dow Corning 193 Surfactant, Dow Corning Q2–5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

Preferred for use in the compositions are silicone surfactants such as dimethiconols or dimethicone copolyols, as mentioned above, which are esterified with fatty acids, such as meadowfoam fatty esters or triglycerides. Examples of meadowfoam fatty esters or triglycerides are disclosed in U.S. Pat. No. 5,646,321, which is hereby incorporated by reference. The silicone surfactants may be silanols such as dimethiconol, which are esterified by the desired fatty acid. In the alternative, the dimethicone copolyol is as mentioned above, wherein the fatty carboxylic acid is reacted with an aliphatic alcohol prior to reaction with the siloxane backbone.

In the preferred compositions of the invention, the nonionic surfactant is an alkoxylated alcohol, or ether, formed by the reaction of a fatty alcohol with ethylene oxide; either alone or in combination with a hydroxy-substituted dimethicone. Particularly preferred is Ceteareth-20, which is the reaction product of a mixture of cetyl and stearyl alcohol with ethylene oxide, and the number of repeating ethylene oxide units in the molecule is 20, and dimethicone copolyol meadowfoamate.

Particularly preferred is a nonionic silicone referred to as trimethylsilylamodimethicone, having the following formula:

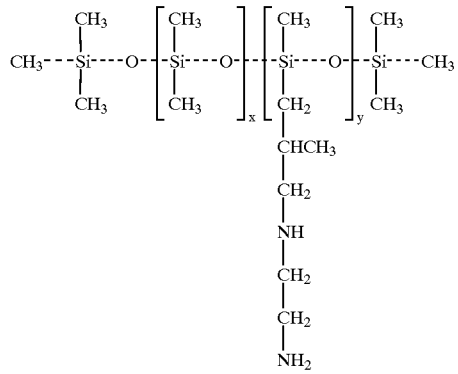

wherein x and y are 1–100,000.

The Organosiloxane Polymer

The compositions of the invention comprise 0.001–20%, preferably 0.001–15%, more preferably 0.1–10% of an organosiloxane polymer. The organosiloxane polymer has both D and T units. The polymer may have any combination of D and T units, either alone or in addition to M and Q units, provided the ratio of D units to T units in the organosiloxane polymer is 10 to 80 D units for every T unit present, preferably 20–60 D units for every T unit, more preferably 25–45 D units for every T unit present. Preferably, the organosiloxane polymers have a molecular weight ranging from about 500 to 1,000,000. The term "M" means a monofunctional siloxy unit, "D" a difunctional unit, "T" a trifunctional unit, and "Q" a quadrifunctional unit. The M, D, T, and Q units may be substituted with functional groups, in which case a prime, e.g. D', is used to indicate substituents other than methyl. Examples of siloxanes suitable for use include those having the following general formulas:

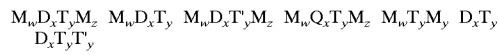

wherein M, D, T, T' and Q are as defined above, and w, x, y, and z are the number of each unit present in the organosiloxane.

The M units have the empirical formula $RRRSiO_{0.5}$, wherein each R is independently H, $C_{1-30}$ straight or branched chain alkyl, which may be substituted with one or more substituents such as halogen or hydroxy, alkoxycarbonyl alkyl, alkylcarbonyl alkoxy, alkylamino, aminoalkylamino, alkylaminoalkylamino, mono-, di- and trialkylaminoalkylamino, polyethyleneoxy-hydroxy, polypropyleneoxy-hydroxy, or phenyl. The D units have the empirical formula $RRSiO_{1.0}$, $RR'SiO_{1.0}$, or $R'R'SiO_{1.0}$, wherein R and R' are each independently as defined above. The T unit has the empirical formula $R'SiO_{1.5}$ or $RSiO_{1.5}$ wherein R and R' are each independently as defined above. The Q unit, if present, has the empirical formula $SiO_{4/2}$.

Preferably, the siloxanes used in the compositions of the invention have the empirical formulas $D_xT'_y$ or $D_xT'_yT''_z$ wherein:

D is $RRSiO_{1.0}$, wherein R is a $C_{1-30}$ straight or branched chain alkyl, preferably methyl, T' is $R'SiO_{1.5}$ wherein R' is aminoalkylaminoalkyl, alkylaminoalkylamino, wherein each alkyl is independently $C_{1-6}$, more preferably R' is aminoethylaminopropyl;

T" is $RSiO_{1.5}$ wherein R alkyl, preferably $C_{1-6}$ alkyl, more preferably methyl; and x/y is 10–80/1; or x/(y+z) is 10–80 to 1.

Most preferably the siloxanes have the formulas I or II, as set forth below:

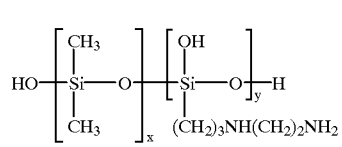

I.

wherein the ratio of x to y is about 20 to 40, most preferably 30–35 to 1. This siloxane can be purchased from GE Silicones under the tradename SM2059, which is a cationic emulsion comprising about 61 parts water, 35 parts of the siloxane of Formula I, 2 parts octoxynol-40, and 2 parts PEG-15 Cocomonium chloride; or

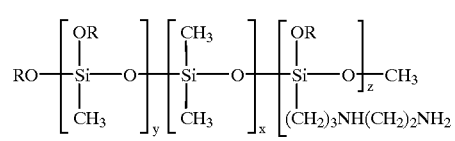

II.

wherein R is a $C_{1-10}$ straight or branched chain alkyl, preferably methyl or ethyl, y is 4–6, x is 50 and z is 1. The silicone of Formula II can be purchased from GE Silicones under the tradename SF 1706, which is a 100% active silicone fluid.

Other Ingredients

It may be desireable to incorporate other ingredients into the hair conditioning compositions of the invention, including film formers, preservatives, humectants, and the like.

Silicones

It may also be desireable to include silicones in the hair conditioning compositions of the invention. Such silicones are known to improve wet and dry combability of hair, exert conditioning effects, and enhance shine and manageability. Suggested ranges of silicone are 0.0001–20%, preferably 0.0005–15%, more preferably 0.001–10% by weight of the total composition.

Suitable silicones include linear and cyclic volatile polydimethylsiloxanes, and linear nonvolatile polydimethylsiloxanes, organosiloxane surfactants, and silicone resins. Volatile silicones are linear or cyclic silicones having a measureable vapor pressure, which is defined as a vapor pressure of at least 2 mm. of mercury at 20° C. Examples of volatile silicones are cyclic silicones having the general formula:

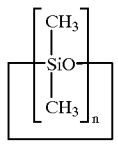

where n=3–7.

Also, linear volatile silicones that may be used in the compositions of the invention have the general formula:

$$(CH_3)_3Si\text{—}O\text{—}[Si(CH_3)_2\text{—}O]_n\text{—}Si(CH_3)_3$$

where n=0–7, preferably 0–5.

The silicone may comprise water insoluble nonvolatile silicone fluids including polyalkyl siloxanes, polyaryl siloxanes, polyalkylaryl siloxane copolymers, and mixtures thereof. Such silicones have the following general formula:

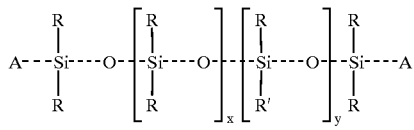

wherein R and R' are each independently alkyl, or aryl, and x and y are each independently 0–100,000 with the proviso that there is at least one of either x or y, and A is siloxy endcap unit. Preferred is where A is methyl, and R and R' are methyl.

Particularly preferred for use in the compositions and methods of the invention are a mixture of silicones of the above formula where in the first silicone, A, R, and R' are lower alkyl, preferably methyl, one of x or y is zero, and the other of x or y is 2–9, preferably 5; and where in the second silicone A, R, and R' are lower alkyl, preferably methyl, one of x or y is zero, and the other of x or y is 10–50, preferably 10–40, more preferably 10–30.

Silicone resins are also suitable for use in the compositions of the invention. Silicone resins are siloxy silicate polymers having the following general formula:

$$[(RR'R'')_3SiO_{1/2}]_x[SiO_2]_y$$

wherein R, R' and R" are each independently a $C_{1-10}$ straight or branched chain alkyl or phenyl, and x and y are such that the ratio of $(RR'R'')_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, which is a blend of about 40–60% volatile silicone and 40–60% trimethylsiloxy silicate Dow Corning 2-0749 in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

Also suitable are silicone esters such as those disclosed in U.S. Pat. No. 4,725,658 and U.S. Pat. No. 5,334,737, which are hereby incorporated by reference. Preferred silicone esters are the liquid siloxy silicates disclosed in U.S. Pat. No. 5,334,737, e.g. diisostearoyl trimethylolpropane siloxysilicate (prepared in Examples 9 and 14 of this patent), and dilauroyl trimethylolpropane siloxy silicate (prepared in Example 5 of the patent), which are commercially available from General Electric under the tradenames SF 1318 and SF 1312, respectively.

Also suitable are silicone graft or block copolymers such as vinyl silicone copolymers having the general formula:

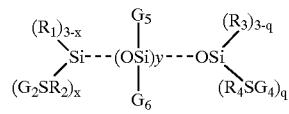

wherein $G_5$ is a monovalent moiety which can independently be the same of different selected from the group consisting of alkyl, aryl, alkaryl, alkoxy, alkylamino, fluoroalkyl, hydrogen, and -ZSA; where A is a vinyl polymeric segment consisting essential of a polymerized free radically polymerizable monomer, and Z is a divalent linking group. Useful divalent linking groups Z include C1–10 alkylene, alkylarylene, arylene, and alkoxyalkylene. Preferably Z is methylene or propylene; and wherein G6 is a monovalent moiety which can independently be the same or different, and is alkyl, aryl, alkaryl, alkoxy, alkylamino, fluoroalkyl, hydrogen, and -ZSA; and wherein $G_2$ is A; and $G_4$ is A; and $R_1$ is a monovalent moiety which is independently the same or different, and is selected from alkyl, aryl, alkaryl, alkoxy, alkylamino, fluoroalkyl, hydrogen, and hydroxyl Preferably $R_1$ is a monovalent moiety which is C1–4 alkyl and hydroxyl, most preferably methyl. $R_2$ can be independently the same or different, and is a divalent linking group such as $C_{1-10}$ alkylene, arylene, alkarylene, and alkoxyalkylene. $R_3$ is a monovalent moiety which can independently be the same or different and is alkyl, aryl, alkaryl, alkoxy, alkylamino, fluoroalkyl, hydrogen, or hydroxyl. $R_4$ can independently be the same or different and are divalent linking groups including $C_{1-10}$ alkylene, arylene, alkarylene, and alkoxyalkylene. The designation x is an integer of 0–3, y is an integer of 5 or greater, and q is an integer of 0–3. Such vinyl silicone graft or block copolymers are disclosed in U.S. Pat. No. 5,468,477, which is hereby incorporated by reference. Preferred is a vinyl silicone copolymer sold by 3-M Company under the tradename VS-80, which also has the CTFA name Polysilicone-8 and the chemical name poly(dimethylsiloxane)-g-polyacrylates.

Polysilicone 8 is soluble in water and miscible with most organic solvents, a colorless to slightly yellow liquid having a specific gravity of 1.013 at 25° C., a viscosity of about 20 centipoise at 25° C., and the polymer has a molecular weight of about 26,000.

Also suitable for use as silicone graft or block copolymers are acryl-silicone graft copolymers as disclosed in U.S. Pat. No. 5,061,481, which is hereby incorporated by reference. These acryl-silicone copolymers may be prepared by the radical polymerization of a dimethylpolysiloxane compound having a polymerizable radical group on one of the molecular chain terminals, and a radically polymerizable monomer comprising predominantly an acrylate or methacrylate or both. The dimethylpolysiloxane having a polymerizable radical group on one of the molecular chain terminals is represented by the following general formula:

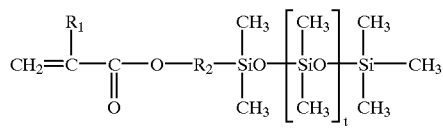

wherein $R_1$ is methyl or hydrogen, $R_2$ is a divalent linear or branched hydrocarbon group having 1–10 carbon atoms and optionally containing one or two ether bonds therein, and 1 is 3–300. Examples of $R_2$ include —$CH_2$—, —$(CH_2)_3$—, —$(CH_2)_5$—, —$(CH_2)_8$—, —$(CH_2)_{10}$—, —$CH_2$—CH($CH_3$)—$CH_2$—, and so on.

Also suitable as a silicone graft or block copolymers are those having a vinyl, methacrylic, or acrylic backbone and pendant siloxane groups and pendant fluorochemical groups. 20 Such polymers preferably comprise comprise repeating A, C, D and optionally B monomers wherein:

A is at least one free radically polymerizable acrylic or methacrylic ester of a 1,1,-dihydroperfluoroalkanol or analog thereof, omega-hydridofluoroalkanols, fluoroalkylsulfonamido alcohols, cyclic fluoroalkyl alcohols, and fluoroether alcohols, B is at least one reinforcing monomer copolymerizable with A, C is a monomer having the general formula $X(Y)_n Si(R)_{3-m} Z_m$ wherein
  X is a vinyl group copolymerizable with the A and B monomers,
  Y is a divalent linking group which is alkylene, arylene, alkarylene, and aralkylene of 1 to 30 carbon atoms which may incorporate ester, amide, urethane, or urea groups,
  n is zero or 1;
  m is an integer of from 1 to 3,
  R is hydrogen, $C_{1-4}$ alkyl, aryl, or alkoxy,
  Z is a monovalent siloxane polymeric moiety; and
D is at least one free radically polymerizable acrylate or methacrylate copolymer, Such polymers and their manufacture are disclosed in U.S. Pat. Nos. 5,209,924 and 4,972,037, which are hereby incorporated by reference.

Preferred is wherein the polymer is a combination of A, C, and D monomers wherein A is a polymerizable acrylic or methacrylic ester of a fluoroalkylsulfonamido alcohol, and where D is a methacrylic acid ester of a $C_{1-12}$ straight or branched chain alcohol, and C is as defined above. Most preferred is a polymer having moieties of the general formula:

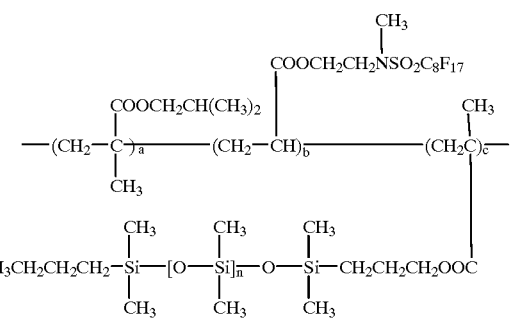

wherein a, b, and c are 1–100,000, and the terminal groups can be $C_{1-20}$ straight or branched chain alkyl, aryl, alkoxy, and the like. These polymers may be purchased from Minnesota Mining and Manfacturing Company under the tradenames "Silicone Plus" polymers. Most preferred is poly (isobutyl methacrylate-co-methyl FOSEA)-g-poly (dimethylsiloxane) which is sold under the tradename SA 70-5 IBMMF.

The preferred compositions of the invention contain 0.0001–10% of a silicone ester, in particular a liquid sioxy silicate which is diisostearoyl trimethylolpropane sioxy silicate.

Oily Conditioning Agents

The compositions of the invention may additionally contain 0.05–10%, preferably 0.1–8%, more preferably 1–7% of an oily conditioning agent which is an organic, nonvolatile oil. The term "nonvolatile" means that the oil does not have a measureable vapor pressure, i.e. has a vapor pressure of less than about 2 mm. mercury at 20° C. Preferably, the nonvolatile oil has a viscosity ranging from 10 to 1,000,000 centipoise at 25° C., preferably 20 to 600,000 centipoise at 25° C.

The oil may comprise esters of the formula RCO—OR' wherein R and R' are each independently a $C_{1-25}$, preferably a $C_{4-20}$ straight or branched chain alkyl, alkenyl or alkoxy-carbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/ caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the C.T.F.A. Cosmetic Ingredient Handbook, First Edition, 1988, which is hereby incorporated by reference.

The oil may also comprise glyceryl esters of fatty acids, or triglycerides, such as castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are glyceryl esters (excluding fats and oils which are glyceryl esters of fatty acids) which are primarily fatty acid mono-di- and triglycerides which are modified by reaction with other alcohols, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Also suitable as the oil are various lanolin derivatives such as acetylated lanolin, acetylated lanolin alcohol, and so on.

Also suitable as the oil are various fluorinated oils are fluoro guerbet esters or perfluropolyethers. Suitable perfluoropolyethers are disclosed in U.S. Pat. Nos. 5,183,589, 4,803,067, 5,183,588 all of which are hereby incorporated by reference. These perfluoropolyethers are commercially available from Montefluos under the trademark Fomblin.

Other suitable oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

Preferred nonvolatile oils are guerbet esters. The term "guerbet ester" means an ester which is formed by the reaction of a guerbet alcohol having the general formula:

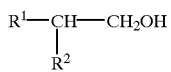

with a carboxylic acid having the general formula:

or

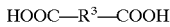

wherein $R^1$ and $R^2$ are each independently a $C_{4-20}$ alkyl and $R^3$ is a substituted or unsubstituted $C_{1-50}$ straight or branched chain saturated alkyl or alkylene, or phenyl, wherein the substituents are halogen, hydroxyl, carboxyl, and alkylcarbonylhydroxy. Preferably, the guerbet ester is a fluoro-guerbet ester which is formed by the reaction of a guerbet alcohol and carboxylic acid (as defined above), and a fluoroalcohol having the following general formula:

$$CF_3-(CF_2)_n-CH_2-CH_2-OH$$

wherein n is from 3 to 40.

Examples of guerbet esters are as set forth in U.S. Pat. No. 5,488,121 which is hereby incorporated by reference. Suitable fluoro-guerbet esters are set forth in U.S. Pat. No. 5,312,968 which is hereby incorporated by reference. Most preferred are fluoro-substituted guerbet esters having the tentative CTFA name fluoro-octyldodecyl meadowfoamate. This ester is sold by Siltech, Norcross, Ga. as Developmental Ester L61125A, under the tradename Silube GME-F; or a cyclic fluoro-guerbet ester sold under the tradename Fluorosil™ by Biosil, and having the chemical name dioctyldodecyl fluoroheptyl citrate.

In addition, the composition may contain 0.001–5%, preferably 0.005–4%, more preferably 0.01–3% by weight of humectant. The humectant is a hygroscopic ingredient that acts to moisturize the hair by attracting water. Suitable humectants are polyhydric and dihydric alcohols such as propylene glycol, glucose, fructose, glycerin, maltitol, and so on. Preferred is wherein the conditioning composition of the invention contains 0.01–3% of a dihydric alcohol, in particular, propylene glycol.

The Method of the Invention

To practice the method for improving fade resistance of color treated hair, the organosiloxane polymer may be incorporated into a variety of aqueous based hair care compositions, such as shampoos, hair conditioners (as mentioned above), oxidative hair dye, compositions, and the like, all of which contain hair treating active agents. Further examples are set forth herein.

SHAMPOOS

Suitable shampoos for use in the method of the invention comprise about 0.1–99% water and 0.1–40% of a cleansing surfactant. In addition, the shampoo compositions may contain ingredients such as cationic conditioning agents, silicones, thickeners, vitamins, preservatives, and the like.

Anionic Surfactants

Suitable cleansing surfactants include anionic, amphoteric, and zwitterionic surfactants. Anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide. The fatty acids may be derived from coconut oil, for example.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sulfones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

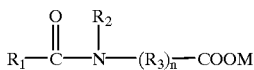

wherein $R_1$ is a $C_{8-24}$ alkyl or alkenyl radical, preferably $C_{10-18}$; $R_2$ is H, $C_{1-4}$ alkyl, phenyl, or —$CH_2COOM$; $R_3$ is $CX_2$— or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

Amphoteric Surfactants

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, tosylate, sulfate, phosphate, or phosphonate.

Suitable amphoteric surfactants may be imidazolinium compounds having the general formula:

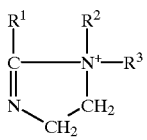

wherein $R_1$ is $C_{8-22}$ alkyl or alkenyl, preferably $C_{12-16}$; $R^2$ is $CH_2CH_2OH$ or $CH_2CH_2OCH_2CH_2COOM$; $R^3$ is hydrogen, $CH_2CH_2OH$, or $CH_2CH_2OCH_2CH_2COOM$. Examples of such materials are marketed under the tradename MIRANOL, by Miranol, Inc.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants include aminoalkanoates of the formula

or iminodialkanoates of the formula:

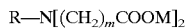

and mixtures thereof; wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-iminodipropionic acid, or mixtures thereof.

Zwitterionic surfactants are also suitable for use in the compositions of the invention. The general formula for such surfactants is:

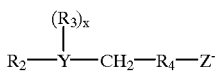

wherein $R_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or mono- or polyhydroxyalkyl group containing about 1 to 3 carbon atoms; X is 1 when Y is a sulfur atom, and 2 when Y is a nitrogen or phosphorus atom; $R_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionics include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido-betaines such as coco dimethyl sulfopropyl betaine, stearyl dimethyl sulfopropyl betaine, and the like.

It may be desireable to incorporate one or more cationic conditioning agents into the compositions, and if so, the types of ingredients and amounts used are the same as those mentioned herein for hair conditioners and the other aqueous based compositions.

Suitable shampoos for use in the practice of the invention include those set forth in U.S. Pat. Nos. 5,672,576 and 5,306,489, both of which is hereby incorporated by reference.

HAIR COLOR COMPOSITIONS

The compositions which may be used in the method of the invention include hair color compositions, comprising about:

0.0001–20% (combined weight) of at least one primary intermediate and at least one coupler for the formation of oxidation dyes, about 0.001–20% of the organosiloxane, about 0.5–20% surfactant, and about 10–65% water.

Primary intermediates and couplers are well known hair coloring ingredients, and include ortho or para substituted aminophenols or phenylenediamines, such as para-phenylenediamines of the formula:

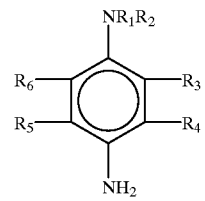

wherein $R_1$ and $R_2$ are each independently hydrogen, $C_{1-6}$ alkyl, or $C_{1-6}$ alkyl substituted with one or more hydroxy, methoxy, methylsulphonylamino, aminocarbonyl, furfuryl, unsubstituted phenyl, or amino substituted phenyl groups; $R_3$, $R_4$, $R_5$, and $R_6$ are each independently hydrogen, $C_{1-6}$ alkyl, $C_{1-6}$ alkoxy, halogen, or $C_{1-6}$ alkyl substituted with one or more hydroxy or amino groups.

Examples of suitable primary intermediates include para-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, ortho-aminophenol, 2-chloro-1,4-diaminobenzene, 2-methoxy-1,4-diaminobenzene, 1-phenylamino-4-aminobenzene, 1-dimethylamino-4-aminobenzene, 1-diethylamino-4- aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropylamino-4-aminobenzene, 2,6-dimethyl-3-methoxy-1,4-diaminobenzene, 1-amino-4-hydroxybenzene, and derivatives thereof, and acid or basic salts thereof.

Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

Suitable couplers include, for example, those having the general formula:

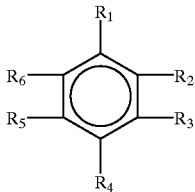

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, catechol, meta-aminophenols, meta-phenylenediamines, and the like, which may be unsubstituted, or substituted on the amino group or benzene ring with alkyl, hydroxyalkyl, alkylamino groups, and the like. Suitable couplers include 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3 [(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, and mixtures thereof.

Preferred couplers include resorcinol, 1-naphthol, 5-amino-o-cresol, 2-methylresorcinol, m-aminophenol, m-phenylenediamine, 1-phenyl-3-methyl-pyrazol-5-one, their salts, or mixtures The surfactants may be anionic, cationic, nonionic, or amphoteric, as mentioned above. Particularly preferred are hair dye compositions as disclosed in U.S. patent application Ser. No. 819,809, filed Mar. 18, 1997, which is hereby incorporated by reference.

PERMANENT WAVE COMPOSITIONS

Permanent wave compositions may be used in the method of the invention. Suitable permanent wave compositions comprise:

0.001–20% of the organosiloxane,
0.01–50% of an agent capable of breaking disulfide bonds.

Examples of agents which are capable of breaking disulfide bonds include thioglycolate and derivatives thereof, cysteamine and derivatives thereof, and similar agents. Examples of suitable permanent wave compositions for use in the method of the invention include those set forth in U.S. Pat. Nos. 5,533,532 and 4,158,704, both of which are hereby incorporated by reference.

The fade resistance of color treated hair may be improved by treating the hair with the aqueous-based hair care composition in a variety of ways.

For example, the organosiloxane may be incorporated into hair conditioner compositions as described above, which are applied to the hair immediately after coloring the hair with oxidative hair color. For example, the hair dye is mixed with an appropriate developer composition, then applied to the hair for an appropriate period of time to cause coloration of the hair, generally about 5 to 35 minutes. The dye is then rinsed from the hair with water and the conditioner applied to the hair for an appropriate period of time, preferably about 0.5 to 20 minutes, and then rinsed from the hair. Preferably, the hair is conditioned with this conditioner immediately after coloring the hair, as well as after every shampoo, in order to maximize fade resistance.

As mentioned herein, the organosiloxane may be incorporated into the oxidative dye composition. Upon coloring the hair the dye composition is applied to the hair, or mixed first with the developer in the appropriate ratios, and then applied to the hair for about 5 to 35 minutes. The hair is then rinsed. If desired a conditioner composition containing the organosiloxane may also be applied to the hair after coloring.

In the case where the organosiloxane is incorporated into a shampoo, the shampoo is used to cleanse the hair in the usual manner. For best results in promoting fade resistance, the shampoo containing the organosiloxane is used on a daily basis, or as often as the individual shampoos his or her hair.

As mentioned, the organosiloxane may be incorporated into permanent wave compositions and used in the method of the invention. In this case, the permanent wave composition is applied to the hair in the appropriate manner in order to curl or straighten the hair, as desired. After 5 to 35 minutes, the permanent wave is rinsed from the hair with water. It may be desired to condition the hair with conditioner containing the organosiloxane as well.

In general, the organosiloxane may be incorporated into any type of composition for application to hair, and will provide improved fade resistance to color treated hair.

The invention also comprises a method for improving hair shine by applying a hair conditioner composition comprising, by weight of the total composition:

(a) a polysiloxane having D and T units wherein the ratio of D units to T units in the polysiloxane is about 10 to 80 D units for every T unit; and (b) a silicone of the formula:

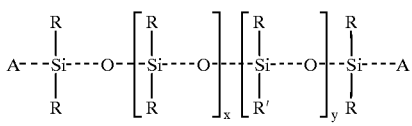

wherein R and R' are each independently alkyl, or aryl, and x and y are each independently 0–100,000 with the proviso that there is at least one of either x or y, and A is siloxy endcap unit.

The hair conditioner composition may be applied after every shampoo, on either normal or color treated hair. The hair conditioner containing this combination of silicones provide improved shine to the hair.

The invention will be further described in connection with the following examples which are set forth for the purposes of illustration only.

EXAMPLE 1

A hair conditioner for use after oxidative dyeing of hair was made according to the following formula:

| | w/w % | |
|---|---|---|
| | 1 | 2 |
| Methyl paraben | 0.20 | 0.20 |
| Propyl paraben | 0.05 | 0.05 |
| Hydroxyethylcellulose | 0.75 | 0.75 |
| Ceteareth alcohol | 2.00 | 2.00 |
| Ceteareth-20 | 0.50 | 0.50 |
| Stearyl alcohol | 1.20 | 1.20 |
| Cetyl alcohol | 1.00 | 1.00 |
| Stearamidopropyl dimethyl amine | 0.75 | 0.75 |
| Cocamidopropyl betaine | 2.00 | 2.00 |
| Behentrimonium chloride | 2.00 | 2.00 |
| Dilinoleamidopropyl dimethylamine dimer dilinoleate | 1.25 | 1.25 |
| Citric acid | 0.16 | 0.16 |
| MPG | 0.001 | 0.001 |
| Panthenol | 0.50 | 0.50 |
| Panthenyl ethyl ether | 0.010 | 0.010 |
| Amodimethicone/tallow trimonium chloride/nonoxynol-10* | 2.00 | 2.00 |
| Diisostearoyl trimethylolpropane siloxysilicate | 0.001 | 0.001 |
| Fragrance | 0.750 | 0.750 |
| Isostearyl citrate/glycolate/lactate/malate | 0.30 | 0.30 |
| Preservative | 0.040 | 0.040 |
| Dimethicone copolyol meadowfoamate | 0.010 | 0.010 |
| GE SM-2059** | 14.300 | — |
| Water | QS | QS |

*a cationic emulsion comprising about 61 parts water, 35 parts amodimethicone having a D to T ratio of about 100 to 1, 2 parts tallowtrimonium chloride, and 2 parts nonoxynol-10.
**a cationic emulsion comprising about 61 parts water, 35 parts amodimethicone having a ratio of D to T units of about 35 to 1, 2 parts octoxynol-40, and 2 parts PEG-15 cocomonium chloride.

Composition 1 provides better color protection on hair than Composition 2.

EXAMPLE 2

An oxidative hair color for use in the method of the invention was made according to the following formula:

| | w/w % | |
|---|---|---|
| | 1 | 2 |
| Erythrobic acid | 0.20 | 0.20 |
| Sodium sulfite | 0.50 | 0.50 |
| Propylene glycol | 4.00 | 4.00 |
| Ethoxydiglycol | 2.00 | 2.00 |
| Tetrasodium EDTA (38% aqueous solution) | 0.80 | 0.80 |
| Ethanolamine | 5.00 | 5.00 |
| Hypnea musciformis extract, gelidiela acarosa extract, sargassum filipendula extract, sorbitol | 0.80 | 0.80 |
| Sodium tinuvin sulfonate, buteth-3, propane tricarboxylic acid | 1.00 | 1.00 |
| Colorant[1] | 1.50 | 1.50 |
| Ammonium lauryl sulfate (28% aqueous solution) | 2.00 | 2.00 |
| Oleic acid | 12.50 | 12.50 |
| Cetearyl alcohol | 4.00 | 4.00 |
| Emulsifying wax | 2.00 | 2.00 |
| Oleth-20 | 1.00 | 1.00 |
| Steareth-21 | 0.70 | 0.70 |
| Meadowfoam seed oil | 0.75 | 0.75 |
| Oleyl alcohol | 0.40 | 0.40 |
| Polyquaternium-10 | 0.20 | 0.20 |
| Polyquaternium-28 | 0.50 | 0.50 |
| Mica, titanium dioxide | 0.30 | 0.30 |
| Hydrolyzed wheat protein | 1.00 | 1.00 |
| Wheat amino acids | 1.00 | 1.00 |
| Fragrance | 0.75 | 0.75 |
| Ammonium hydroxide (27.5% aqueous solution) | 4.50 | 4.50 |
| Amodimethicone[2] | 5.75 | — |
| Amodimethicone[3] | — | 2.00 |
| Water | QS | QS |

[1]mixture of primary intermediates and couplers to provide light auburn, dark brown, light brown color.
[2]a cationic emulsion comprising about 61 parts water, 35 parts amodimethicone having a ratio of D to T units of about 35 to 1, 2 parts octoxynol-40, and 2 parts PEG-15 cocomonium chloride.
[3]amine functional silicone fluid of Formula II, above, wherein R is $OCH_3$ sold by General Electric under the tradename SF 1706, which has a ratio of D to T units of about 10 to 1 respectively.

The compositions were made by mixing the ingredients and heating to 60° C. with stirring. The resulting compositions were smooth gels. When used, the composition was mixed with a developer solution which contained hydrogen peroxide. The mixture was applied to hair and left on the hair for 20 to 30 minutes.

EXAMPLE 3

A curling lotion for use in the method of the invention was made according to the following formula:

| | w/w % |
|---|---|
| Polyquaternium-10 | 0.01 |
| Polyquaternium-6 | 4.10 |
| Pentasodium pentetate | 0.20 |
| Ammonium thioglycolate (60% aqueous solution) | 20.00 |
| Ammonium hydroxide (27.5%) | 3.39 |
| Diammonium dithioglycolate (40% aqueous solution) | 2.00 |
| Propylene glycol | 6.00 |
| Laureth-23 | 0.60 |
| Fragrance | 0.10 |
| Hydrolyzed collagen (55% aqueous solution) | 0.05 |
| Glycine | 0.05 |
| D&C Yellow #10 | 0.0002 |
| Amodimethicone* | 5.75 |
| Water | QS |

*a cationic emulsion comprising about 61 parts water, 35 parts amodimethicone having a ratio of D to T units of about 35 to 1, 2 parts octoxynol-40, and 2 parts PEG-15 cocomonium chloride.

After application to hair and rinse out, the hair felt smooth, soft, and easy to comb.

EXAMPLE 4

Comparative tests were conducted with five different formulas on human hair swatches containing a 95% gray blend hair swatches as follows:

Experiment 1: Nine hair swatches of each color (light auburn, light brown, medium brown, and dark brown) were treated with a composition having the following formula

|  | w/w % 1 |
|---|---|
| Erythrobic acid | 0.20 |
| Sodium sulfite | 0.50 |
| Propylene glycol | 4.00 |
| Ethoxydiglycol | 2.00 |
| Tetrasodium EDTA (38% aqueous solution) | 0.80 |
| Ethanolamine | 5.00 |
| Hypnea musciformis extract, gelidiela acarosa extract, sargassum filipendula extract, sorbitol | 0.80 |
| Sodium tinuvin sulfonate, buteth-3, propane tricarboxylic acid | 1.00 |
| Colorant[1] | 1.50 |
| Ammonium lauryl sulfate (28% aqueous solution) | 2.00 |
| Oleic acid | 12.50 |
| Cetearyl alcohol | 4.00 |
| Emulsifying wax | 2.00 |
| Oleth-20 | 1.00 |
| Steareth-21 | 0.70 |
| Meadowfoam seed oil | 0.75 |
| Oleyl alcohol | 0.40 |
| Polyquaternium-10 | 0.20 |
| Polyquaternium-28 | 0.50 |
| Mica, titanium dioxide | 0.30 |
| Hydrolyzed wheat protein | 1.00 |
| Wheat amino acids | 1.00 |
| Fragrance | 0.75 |
| Ammonium hydroxide (27.5% aqueous solution) | 4.50 |
| Water | QS | by mixing 1 part of Formula X with 1.5 parts of a developer composition* and applying to the hair for about 25 minutes. The composition was then rinsed out with water until the dye was completely removed. The hair conditioning composition of Example 1, Formula 2 was applied to the hair for 2 minutes and then rinsed out with water until completely removed. (Dyed hair swatches–conditioner containing no organosiloxane)

Experiment 2: Nine hair swatches of each color (light auburn, light brown, medium brown, dark brown) were treated with the composition Formula X by mixing Formula X 1:1.5 with a developer composition**. The composition was applied to the swatches for 25 minutes, then rinsed out with water until the dye was completely removed. The hair conditioning composition of Example 1, Formula 2, was applied to the wet hair for 2 minutes. The composition was rinsed out of the hair with water until completely removed. (Dyed hair swatches+conditioner containing no organosiloxane)

Experiment 3: Nine hair swatches of each color (light auburn, light brown, medium brown, dark brown) were treated with the composition of Formula X by mixing the composition 1:1.5 with a developer composition**. The composition was applied to the swatches for 25 minutes, then rinsed out with water until the dye was completely removed. The hair conditioning composition of Formula 1, Example 1, was applied to the wet hair and allowed to remain for about 2 minutes. The composition was rinsed out of the hair with water until completely removed. (Dyed hair swatches+conditioner with organosiloxane)

Experiment 4: Nine hair swatches of each color (light auburn, light brown, medium brown, dark brown) were treated with the composition of Formula X by mixing the composition 1:1.5 with a developer composition***. The mixture was applied to the swatches for 25 minutes, then rinsed out with water until the dye was completely removed. The hair conditioning composition of Formula 1, Example 1, was applied to the wet hair and allowed to remain for 2 minutes. The composition was rinsed out of the hair with water until completely removed. (Dyed hair swatches+conditioner with organosiloxane)

Experiment 5: Nine hair swatches of each color (light auburn, light brown, medium brown, dark brown) were treated with the composition of Formula 2, Example 2 by mixing the composition 1:1 with a developer composition**. The mixture was applied to the swatches for 25 minutes, then rinsed out with water until the dye was completely removed. The conditioner composition of Formula 1, Example 1 was applied to the wet hair for 2 minutes. The composition was rinsed out of the hair until completely removed. (Dyed hair swatches+conditioner with organosiloxane)

|  | w/w % |
|---|---|
| *The developer had the following formula: |  |
| Methyl paraben (preservative) | 0.05 |
| EDTA (chelating agent) | 0.02 |
| Mineral oil (oil) | 0.60 |
| Cetearyl alcohol/ceteareth-20 (80:20) (emulsifier) | 3.75 |
| Cyclomethicone/trimethylsiloxysilicate (50:50) (silicone conditioner) | 0.01 |
| Cetearyl alcohol (opacifier) | 0.40 |
| Trimethylsilylamodimethicone (silicone conditioner) | 2.00 |
| Disodium phosphate (pH adjuster) | 0.03 |
| Phosphoric acid (pH adjuster) | 0.03 |
| Hydrogen peroxide (35% solution in water) | 25.70 |
| Steareth-10 allyl ether/acrylate copolymer (anionic polymer) | 0.35 |
| Water | QS |
| **The developer had the following formula: |  |
| Methyl paraben (preservative) | 0.05 |
| EDTA (chelating agent) | 0.02 |
| Mineral oil (oil) | 0.60 |
| Cetearyl alcohol/ceteareth-20 (80:20) (emulsifier) | 3.75 |
| Cyclomethicone/trimethylsiloxysilicate (50:50) (silicone conditioner) | 0.01 |
| Cetearyl alcohol (opacifier) | 0.80 |
| Trimethylsilylamodimethicone blend[1] (silicone conditioner) | 1.00 |
| Disodium phosphate (pH adjuster) | 0.03 |
| Phosphoric acid (pH adjuster) | 0.04 |
| Hydrogen peroxide (35% solution in water) | 18.00 |
| Steareth-10 allyl ether/acrylate copolymer (anionic polymer) | 0.01 |
| Water | QS |
| ***the developer had the following formula: |  |
| Methyl paraben (preservative) | 0.05 |
| EDTA (chelating agent) | 0.02 |
| Mineral oil (oil) | 0.60 |
| Cetearyl alcohol/ceteareth-20 (80:20) (emulsifier) | 3.75 |
| Cyclomethicone/trimethylsiloxysilicate (50:50) (silicone conditioner) | 0.01 |
| Cetearyl alcohol (opacifier) | 0.80 |
| Trimethylsilylamodimethicone blend[1] (silicone conditioner) | 2.00 |
| Disodium phosphate (pH adjuster) | 0.03 |
| Phosphoric acid (pH adjuster) | 0.04 |
| Hydrogen peroxide (35% solution in water) | 18.00 |
| Steareth-10 allyl ether/acrylate copolymer (anionic polymer) | 0.01 |
| Water | QS |

[1]Trimethylsilylamodimethicone, C11–13 pareth-7, laureth-9, trideceth-12, and glycerin.

EXAMPLE 5

One light auburn, light brown, and dark brown hair swatch was retained from the swatches of Experiments 1–5 for a control. The remaining eight hair swatches of each color treated according to Experiments 1–5 were shampooed three times using a 12% ammonium lauryl sulfate solution in water. Four of these tresses were further shampooed for a total of twenty times. For each shampoo, the solution was applied to the swatch and shampooed from 0.5 to 1 minute. The swatch was rinsed with water to completely remove the shampoo, and patted dry. Swatches with no shampoo treatment (control tresses), those shampooed three times and those shampooed twenty times, were evaluated by trained hair color panelists. The panelists evaluated each swatch in comparison to the control swatch of the same color, and assessed whether the shampooings caused no change, barely noticeable change, noticeable change, or very noticeable change in hair color intensity.

EXAMPLE 6

The results of tests conducted in Example 5 are as follows. Each number represents the average number of panelists (n=9) who stated that the tress evaluated exhibited barely noticeable, noticeable, or very noticeable change in color intensity when compared with the control tress with 0=no change, 1=barely noticeable change, 2=noticeable change, and 3=very noticeable change.

|  | After 3 shampoos | | | | | After 20 shampoos | | | | |
| --- | --- | --- | --- | --- | --- | --- | --- | --- | --- | --- |
|  | 1 | 2 | 3 | 4 | 5 | 1 | 2 | 3 | 4 | 5 |
| Light auburn | 1.33 | 0.77 | 1.22 | 0.55 | 1.44 | 2.00 | 1.66 | 2.44 | 1.44 | 2.11 |
| Light brown | 1.44 | 1.66 | 1.44 | 1.22 | 0.66 | 2.22 | 2.00 | 2.33 | 1.77 | 1.44 |
| Medium brown | 2.00 | 2.22 | 2.00 | 0.77 | 1.33 | 2.00 | 2.66 | 2.33 | 1.00 | 1.66 |
| Dark Brown | 1.55 | 1.00 | 1.33 | 1.66 | 1.33 | 1.88 | 1.11 | 1.55 | 2.33 | 1.88 |
| (mean) X = | 1.58 | 1.41 | 1.49 | 1.05 | 1.19 | 2.02 | 1.85 | 2.16 | 1.63 | 1.77 |

The above results illustrate that the tresses treated with compositions containing the organosiloxane having D and T units wherein the ratio of D to T units in the siloxane is about 10 to 80 D units for every T unit, exhibited improved resistance to color fading.

EXAMPLE 7

Panelists were then asked to evaluate each tress treated according to Example 5 and indicate whether there was a change in the tonality of the color. The results are as follows. Each number represents the average number of panelists (n=9) who stated that the tress evaluated exhibited no change, barely noticeable, noticeable, or very noticeable change in tonality when compared with the control tress, with 0=no change, 1=barely noticeable change, 2=noticeable change, and 3=very noticeable change.

|  | After 3 shampoos | | | | | After 20 shampoos | | | | |
| --- | --- | --- | --- | --- | --- | --- | --- | --- | --- | --- |
|  | 1 | 2 | 3 | 4 | 5 | 1 | 2 | 3 | 4 | 5 |
| Light auburn | 1.22 | 0.66 | 1.22 | 0.66 | 1.22 | 2.00 | 1.88 | 2.11 | 1.44 | 1.88 |
| Light brown | 1.33 | 1.44 | 1.33 | 1.11 | 1.00 | 2.22 | 1.88 | 2.44 | 1.11 | 1.33 |
| Medium brown | 1.66 | 2.11 | 1.88 | 0.66 | 1.11 | 1.88 | 2.66 | 2.44 | 1.11 | 1.33 |
| Dark Brown | 1.44 | 1.11 | 1.33 | 1.11 | 1.11 | 2.00 | 1.77 | 1.88 | 2.44 | 1.77 |
| (mean) X = | 1.41 | 1.33 | 1.44 | 0.88 | 1.11 | 2.02 | 2.04 | 2.21 | 1.52 | 1.57 |

As illustrated by the above results, the swatches treated with compositions containing the organosiloxanes having D and T units wherein the ratio of D to T unites in the siloxane is about 10 to 80 D unit for every T unit, exhibited improved resistance, i.e. resistance to change in color tonality.

EXAMPLE 8

Panelists were then asked to evaluate tresses treated according to Example 4, Experiment 1 ("1") and Example 4, Experiment 4 ("4"), above, and indicate whether there was a change in the tonality of the color. The results are as follows. Each number represents the average number of panelists (n=9) who stated that the tress evaluated exhibited no change, barely noticeable, noticeable, or very noticeable change in tonality when compared with the control tress, with 0=no change, 1=barely noticeable change, 2=noticeable change, and 3=very noticeable change.

|  | After 3 shampoos | | After 20 shampoos | |
| --- | --- | --- | --- | --- |
|  | 1 | 4 | 1 | 4 |
| Light auburn | 1.13 | 0.53 | 2.20 | 1.60 |
| Light brown | 1.20 | 1.40 | 2.13 | 1.67 |
| Medium brown | 1.67 | 0.87 | 1.93 | 1.13 |
| Dark Brown | 1.40 | 1.20 | 2.07 | 2.47 |
| Champagne Brown | 1.33 | 1.44 | 2.00 | 1.44 |
| Soft black | 1.22 | 0.89 | 1.56 | 1.22 |
| Light ash brown | 2.11 | 1.89 | 2.78 | 2.44 |
| Extra light ash brown | 1.78 | 1.11 | 2.67 | 2.11 |
| (mean) X= | 1.48 | 1.17 | 2.15 | 1.76 |

As illustrated by the above results, the swatches treated with compositions containing the organosiloxanes having D and T units wherein the ratio of D to T unites in the siloxane is about 10 to 80 D unit for every T unit, exhibited improved resistance, i.e. resistance to change in color tonality

EXAMPLE 9

Panelists were then asked to evaluate tresses treated according to Example 4, Experiment 1 ("1") and Example 4, Experiment 4 ("4"), above, and indicate their opinion on the stability of color intensity in the color treated hair. The results are as follows. Each number represents the average number of panelists (n=9) who stated that the tress evaluated exhibited no change, barely noticeable, noticeable, or very noticeable change in tonality when compared with the control tress, with 0=no change, 1=barely noticeable change, 2=noticeable change, and 3=very noticeable change.

|  | After 3 shampoos | | After 20 shampoos | |
| --- | --- | --- | --- | --- |
|  | 1 | 4 | 1 | 4 |
| Light auburn | 1.40 | 0.47 | 2.20 | 1.80 |
| Light brown | 1.40 | 1.20 | 2.20 | 1.67 |
| Medium brown | 1.93 | 0.67 | 2.20 | 1.07 |
| Dark Brown | 1.47 | 1.60 | 1.80 | 2.40 |
| Champagne Brown | 1.22 | 1.11 | 2.00 | 1.22 |
| Soft black | 1.11 | 0.67 | 1.67 | 1.11 |
| Light ash brown | 2.11 | 1.89 | 2.67 | 2.11 |
| Extra light ash brown | 2.00 | 1.44 | 2.67 | 2.22 |
| (mean) X= | 1.58 | 1.13 | 2.18 | 1.70 |

As illustrated by the above results, the swatches treated with compositions containing the organosiloxanes having D and T units wherein the ratio of D to T unites in the siloxane is about 10 to 80 D unit for every T unit, exhibited improved color intensity, i.e. resistance to change in color intensity.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for improving the fade resistance of color treated hair comprising applying to the hair an aqueous based hair care composition containing one or more hair treating active ingredients and a siloxane having difunctional units and trifunctional units, wherein the ratio of difunctional units to trifunctional units in the siloxane is about 10 to 80 difunctional units for every trifunctional unit.

2. The method of claim 1 wherein the ratio of D to T units in the siloxane is 20–60 D units for every T unit.

3. The method of claim 1 wherein the aqueous based hair care composition is a hair conditioner.

4. The method of claim 1 wherein the aqueous based hair care composition is a hair dye composition.

5. The method of claim 4 wherein the hair dye composition comprises, by weight of the total composition:

0.001–20% of the siloxane, 0.5–20% surfactant, and

10–65% water.

6. The method of claim 1 wherein the aqueous based hair care composition comprises a shampoo.

7. The method of claim 6 wherein the shampoo composition comprises, by weight of the total composition:

0.1–40% of a cleansing surfactant, 0.1–99% water.

8. The method of claim 1 wherein the aqueous based hair care composition comprises a permanent wave composition.

9. A method for improving the fade resistance of color treated hair comprising the steps of:

a) coloring the hair with an aqueous based hair dye composition, and then b) conditioning the hair with an aqueous based conditioning composition containing an organosiloxane having difunctional units and trifunctional units, wherein the ratio of difunctional to trifunctional units in the organosiloxane polymer is 10–80 difunctional units for every trifunctional unit.

* * * * *